(12) United States Patent
Konicek

(10) Patent No.: US 9,649,189 B2
(45) Date of Patent: May 16, 2017

(54) REINFORCED BIOLOGICAL CONSTRUCT AND METHOD OF REINFORCING BIOLOGICAL CONSTRUCT

(75) Inventor: John Konicek, Naples, FL (US)

(73) Assignee: ARTHREX, INC., Naples, FL (US)

( * ) Notice: Subject to any disclaimer, the term of this patent is extended or adjusted under 35 U.S.C. 154(b) by 330 days.

(21) Appl. No.: 13/207,563

(22) Filed: Aug. 11, 2011

(65) Prior Publication Data

US 2012/0046746 A1 Feb. 23, 2012

Related U.S. Application Data

(60) Provisional application No. 61/376,109, filed on Aug. 23, 2010.

(51) Int. Cl.
*A61F 2/08* (2006.01)
*A61B 17/04* (2006.01)

(52) U.S. Cl.
CPC ........ *A61F 2/08* (2013.01); *A61B 2017/0404* (2013.01); *A61F 2230/0065* (2013.01)

(58) Field of Classification Search
CPC ....................................................... A61F 2/08
USPC ............................................ 623/13.11–13.2
See application file for complete search history.

(56) References Cited

U.S. PATENT DOCUMENTS

| | | | | |
|---|---|---|---|---|
| 3,545,008 A * | 12/1970 | Bader, Jr. | ................... | 623/13.15 |
| 6,517,578 B2 * | 2/2003 | Hein | ......................... | 623/13.13 |
| 8,591,544 B2 | 11/2013 | Jolly et al. | | |
| 2001/0051815 A1 * | 12/2001 | Esplin | .......................... | 606/232 |
| 2002/0165611 A1 * | 11/2002 | Enzerink et al. | .......... | 623/13.11 |
| 2003/0229396 A1 * | 12/2003 | Andrews | ................... | A61F 2/08 623/13.13 |
| 2005/0154446 A1 * | 7/2005 | Phillips | ..................... | A61F 2/07 623/1.13 |
| 2007/0239275 A1 * | 10/2007 | Willobee | .................. | A61F 2/08 623/13.17 |
| 2007/0250163 A1 * | 10/2007 | Cassani | ...................... | 623/13.17 |
| 2008/0195148 A1 * | 8/2008 | Cook et al. | ................... | 606/232 |
| 2010/0256677 A1 * | 10/2010 | Albertorio | ......... | A61B 17/0401 606/232 |
| 2012/0253465 A1 | 10/2012 | Missos | | |

* cited by examiner

*Primary Examiner* — Yashita Sharma
(74) *Attorney, Agent, or Firm* — Carlson, Gaskey & Olds

(57) ABSTRACT

A reinforced graft construct for repairing a tendon or ligament formed by inserting a piece of material, such as suture, through the graft lengthwise. The material may be inserted along only a portion of the graft or along the entire graft. The material may be a reinforcement (reinforcing) material such as suture, tape, weave, or mesh passed lengthwise through the graft (for example, along the center of the graft). The ends of the graft may be whipstiched to provide additional fixation when implanted. The material may be bioabsorbable such that it will resorb away after a period of time in the body.

19 Claims, 13 Drawing Sheets

REINFORCED BIOLOGICAL CONSTRUCT AND METHOD OF REINFORCING BIOLOGICAL CONSTRUCT

CROSS-REFERENCE TO RELATED APPLICATIONS

This application claims the benefit of U.S. Provisional Application No. 61/376,109, filed Aug. 23, 2010, the entire disclosure of which is incorporated by reference herein.

FIELD OF THE INVENTION

The present invention relates to the field of surgery and, more particularly, to a construct for tendon or ligament repair or reconstruction, to a method of ligament or tendon repair or reconstruction, and also to a method of graft preparation for attachment to bone.

BACKGROUND OF THE INVENTION

Reconstructive surgeries, particularly tendon or ligament reconstruction, are well-known in the art. In general, these methods involve repairing a tendon or ligament by stitching it together or using a graft to repair the tendon or ligament. ACL repairs involve drilling a tunnel through the tibia, drilling a closed tunnel (socket) into the femur, inserting a substitute ACL graft into the tunnels, and securing the graft to the walls of the tibial and femoral tunnels using interference screws or the like. Tensioning and fixation of the graft in the tunnel is important for optimal results. A need exists for a method of re-attachment of soft tissue to bone which allows the graft to be securely placed in the bone tunnel and properly tensioned until natural reattachment occurs.

Repairs of other tendons or ligaments, such as the Achilles tendon, require trying to reattach the torn pieces of the existing tendon back together. This can be difficult to accomplish when the tendon ends are weaker because of the tear. The stitches can rip through the tendon at the repair site. A need exists for reinforcing the torn tendon at the repair site.

BRIEF SUMMARY OF THE INVENTION

The present invention provides a construct and method for attachment of tendon/ligament/graft to bone using a reinforced tendon/ligament/graft construct for repair or reconstruction. The reinforced construct includes a tendon/ligament/graft with a material such as suture, tape, weave, or mesh passed lengthwise through the center of the construct with the ends of the construct being whipstiched to provide additional fixation when implanted. The material may be absorbable or non-absorbable.

Other features and advantages of the present invention will become apparent from the following description of the invention which refers to the accompanying drawings.

DETAILED DESCRIPTION OF THE INVENTION

The present invention provides techniques and constructs for ligament or tendon repair or graft preparation that provide simpler reconstruction techniques and improved graft fixation.

According to the techniques of the present invention, a reinforced construct (for example, a reinforced graft, ligament or tendon construct) for repairing a tendon or ligament is formed by inserting a piece of material (such as suture) through the graft lengthwise. The material may be inserted along only a portion of the graft or along the entire graft. For example, the material may be a reinforcement (reinforcing) material such as suture, tape, weave, or mesh passed lengthwise through the graft (for example, through the center of the graft and along the longitudinal axis of the graft). The ends of the graft may be whipstiched to provide additional fixation when implanted.

The reinforcing material may be bioabsorbable such that it will resorb away after a period of time in the body. The ends of the graft may be whipstitched as is known in the art to provide for added strength of the graft for better fixation.

The reinforced graft construct may also be formed into a loop with at least one fixation device attached to the reinforced graft construct (for example, with a fixation device on each end) for various repairs such as ACL repairs.

Figure 1:
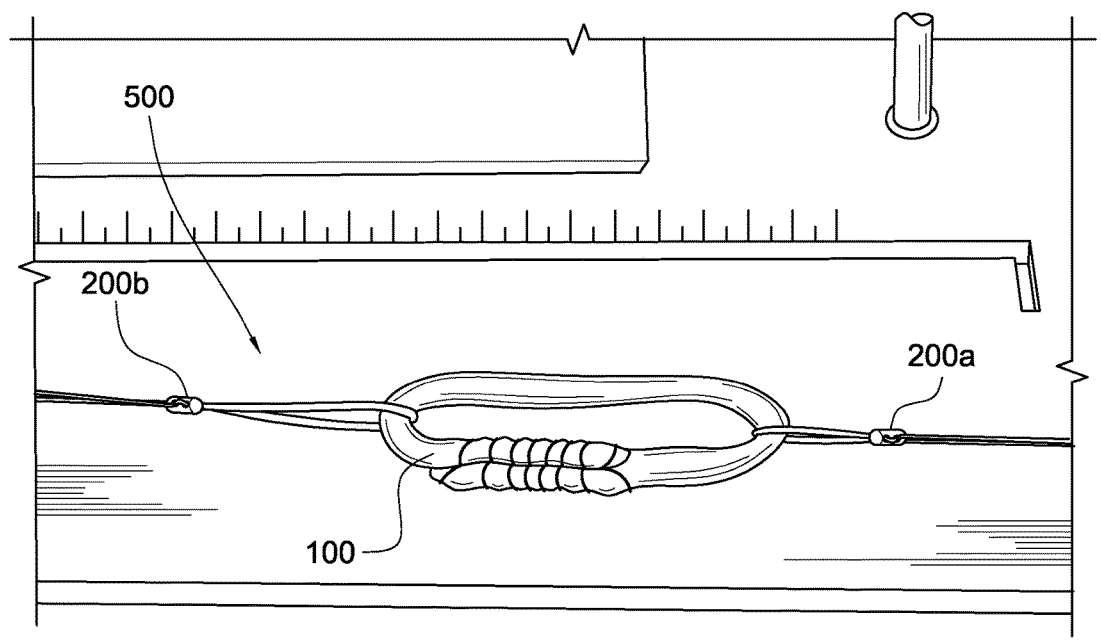
FIG. 1 illustrates a reinforced assembly including a reinforced continuous graft loop construct with an overlapped whipstiched section according to an embodiment of the present invention and with two fixation members for ACL reconstruction.

FIG. 1 illustrates a final reinforced assembly 500 comprising a reinforced loop construct 100 of the present invention with two fixation devices 200a, 200b attached thereto. As detailed below, the reinforced loop construct 100 is formed of a loop of biological construct 10 (such as graft, ligament or tendon) with ends 12, 14 attached together and with a reinforcement material 30 extending longitudinally along at least a portion of the length of the biological construct 10. At least one fixation device may be optionally attached to the reinforced loop construct 100. As detailed below, the ends 12, 14 may be attached (brought together) in an overlapping or non-overlapping manner and they may be stitched to form additional reinforced sections.

Although the embodiments below will be described with reference to particular materials and compositions such as graft 10 or suture 30, it must be understood that the invention is not limited to these particular exemplary embodiments and encompasses any biological construct (such as graft, tendon, ligament, or combinations thereof) that can be reinforced with any reinforcement material (such as suture, tape, mesh, or combinations thereof).

An exemplary method of forming the reinforced loop construct 100 (reinforced graft construct 100) of FIG. 1 is detailed below with reference to FIGS. 2A-2G.

Figure 2A:
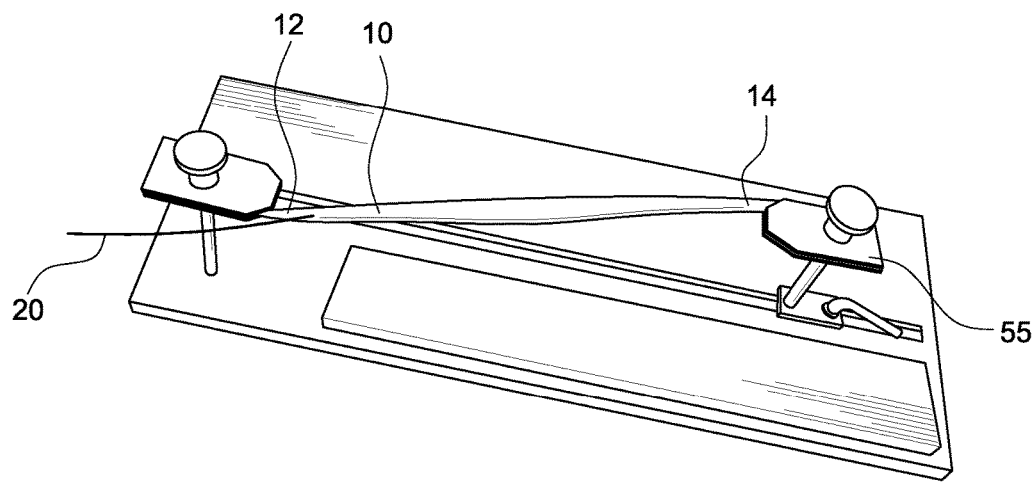
FIGS. 2A-2G illustrate subsequent steps for making the reinforced continuous graft loop of FIG. 1.

FIG. 2A illustrates biological construct 10 (such as graft, ligament or tendon 10) secured in a prep-station 55 with an exemplary nitinol passing wire 20 inserted therethrough. Biological construct 10 having a first end 12 and a second end 14 is secured lengthwise to prep-station 55. A nitinol passing wire 20 is inserted into one end of biological construct 10. A length of reinforcement material 30 (suture or tape 30), such as Fiberwire® or FiberTape® manufactured by Arthrex, Inc. Naples, Fla. is attached to the passing wire 20.

Figure 2B:
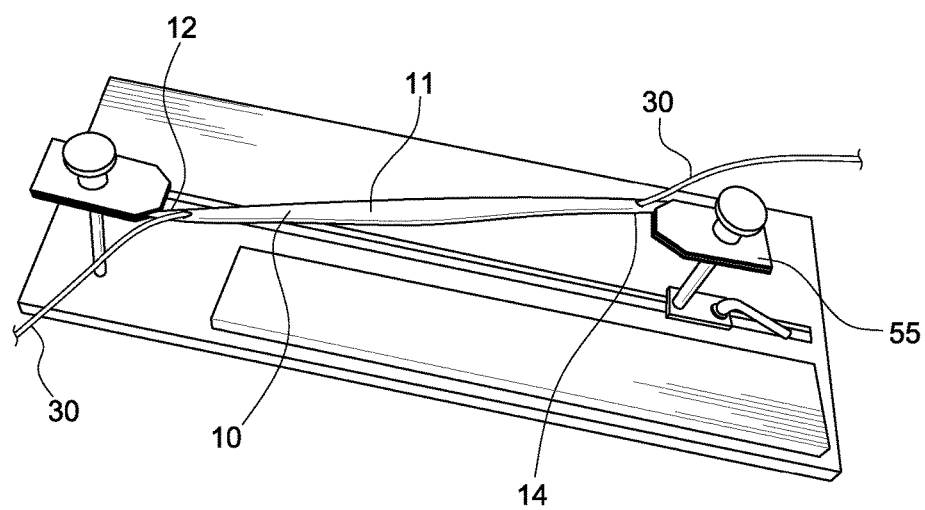

FIG. 2B illustrates the nitinol wire pulling the tape 30 (FiberTape® 30) through the biological construct 10. The passing wire 20 is pulled through the biological construct 10 to the second end 14. As the passing wire 20 travels through the biological construct, the suture 30 follows until the passing wire has passed completely through the biological construct leaving only the suture 30 extending from the first end 12 to the second end 14 to form reinforced biological construct 11 (i.e., tendon 10 reinforced with suture or tape 30).

Figure 2C:
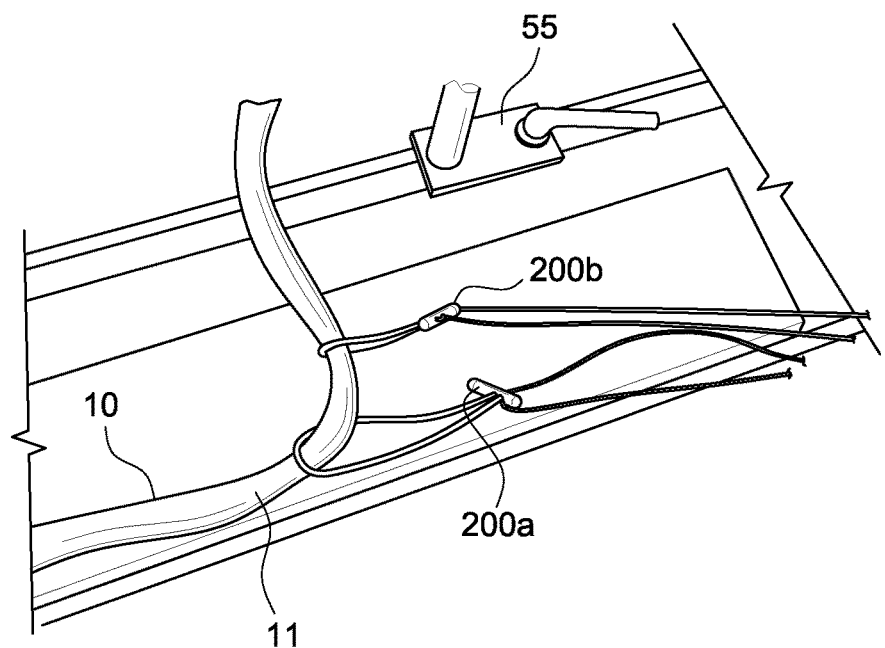

FIG. 2C: In one embodiment, the biological construct 10 may be used for an arthroscopic repair such as ACL repair. A variety of fixation devices 200a, 200b for the tibia and/or femur may be inserted onto the reinforced biological construct 11 (or attached to it) for ACL repair with fixation at both ends (and prior to the loop formation). Examples of fixation devices include a loop with a button (such as the RetroButton manufactured by Arthrex Inc.) or an adjustable loop with button (such as the ACL Tightrope manufactured by Arthrex Inc.). FIG. 2C illustrates a RetroButton 200a and an ACL Tightrope 200b passed over the reinforced biological construct 11 and prior to the loop formation.

Figure 2D:
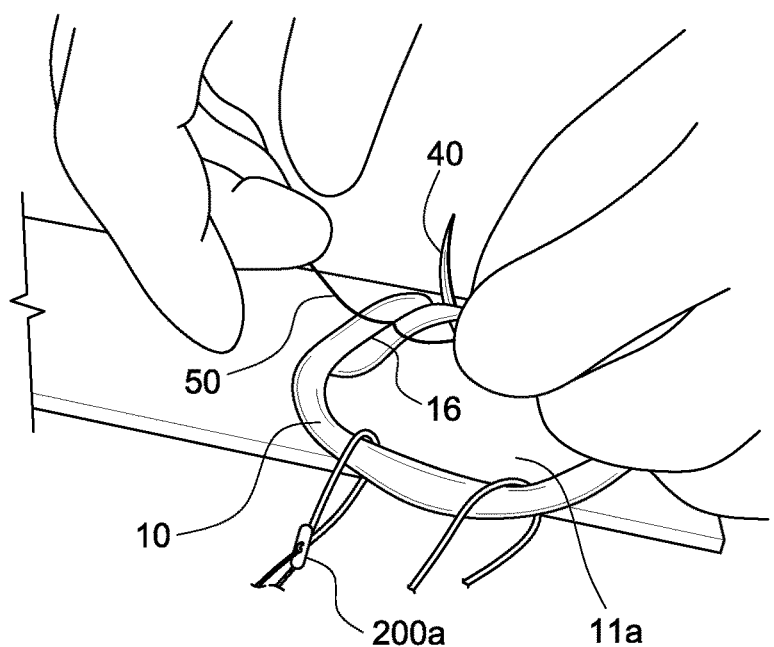

FIG. 2D: The reinforced biological construct 11 is doubled over so that the first end 12 and the second end 14 overlap and form a reinforced loop 11a. The first and second ends 12, 14 are stitched together using a needle 40 and suture 50 to whipstitch through the biological construct 10 and the suture or tape 30 in the overlapping section 16, to create reinforced loop construct 100 (reinforced graft, ligament or tendon loop construct 100). FIG. 2D illustrates an exemplary #2 Fiberwire® 50 with a tapered needle 40 used to whipstitch the overlapping section.

Figure 2E:
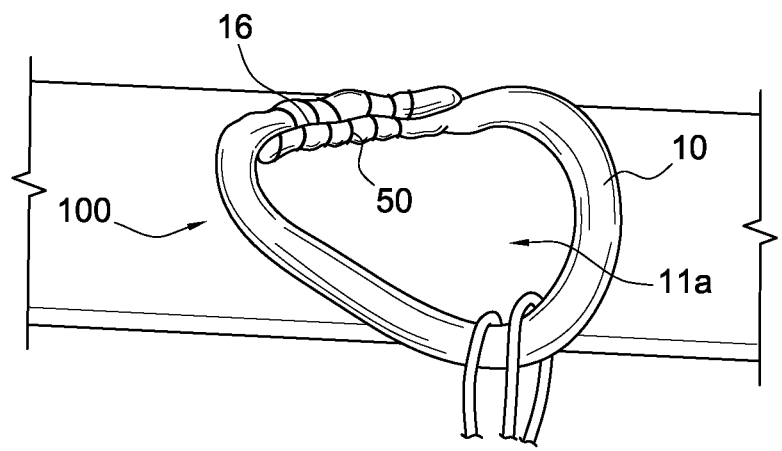
Figure 2F:
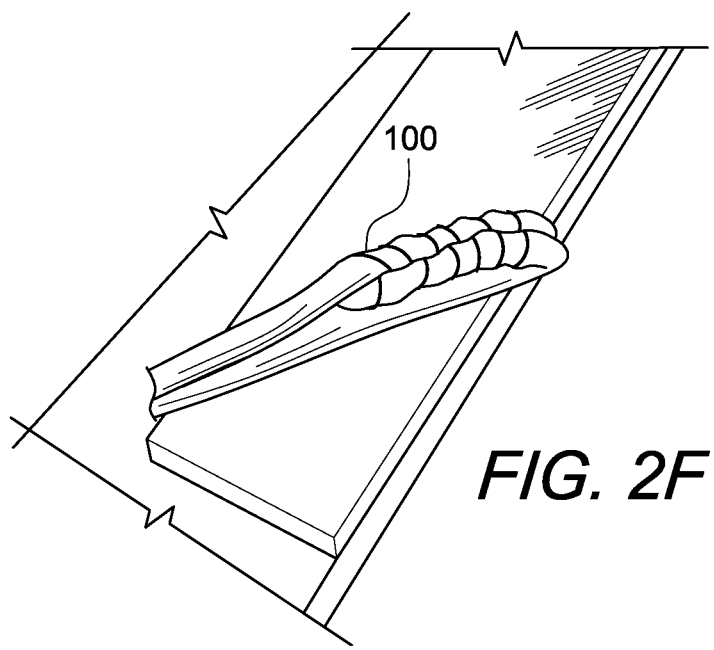

FIGS. 2E-F: The whipstitching continues (FIG. 2E) and is completed with a knot (for example, a six-thrown surgeon's knot shown in FIG. 2F) to complete the reinforced loop construct 100.

Figure 2G:
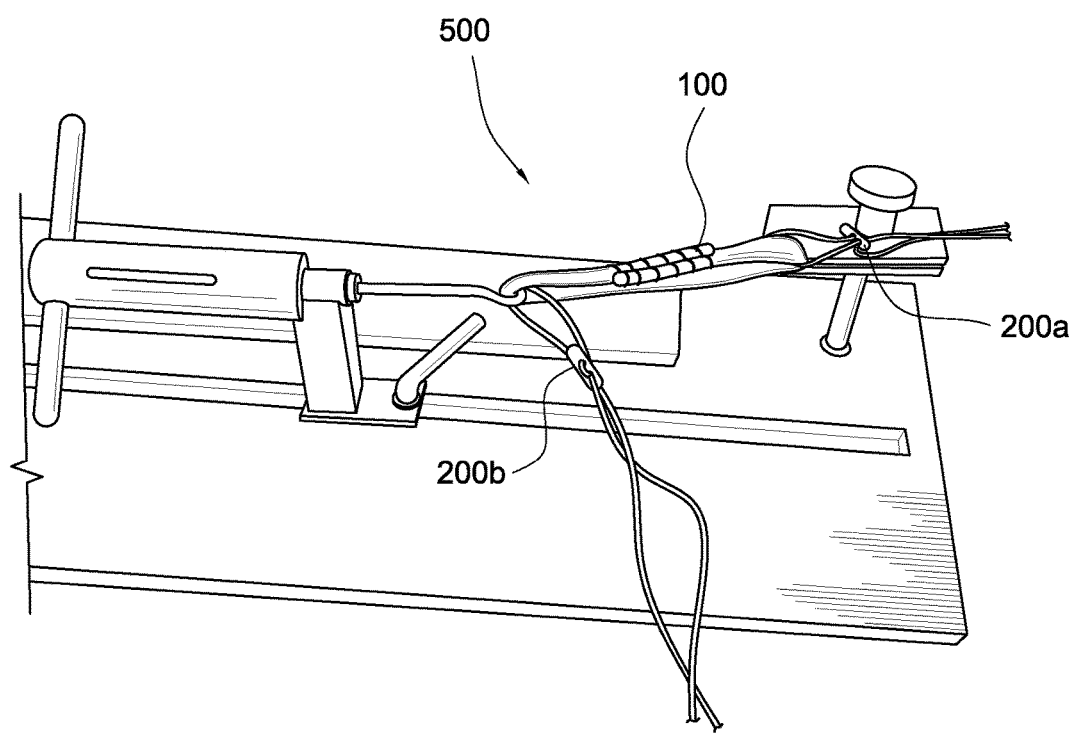

FIG. 2G: Once the whipstitching of the reinforced graft loop construct 100 is completed, the reinforced assembly 500 is pre-tensioned to 20 pounds for use in ACL repair. Depending on the type of repair the construct is being used for will determine the amount of pre-tensioning, which may be up to 50 pounds.

Although the above method was described using whipstitching, any type of suturing/stitching that would attach the first and second ends of the biological construct 10 (tendon 10) together could be used. Additionally, the suture that is passed lengthwise through the biological construct 10 may be an absorbable suture that would resorb away after a length of time in the body.

Figure 3:
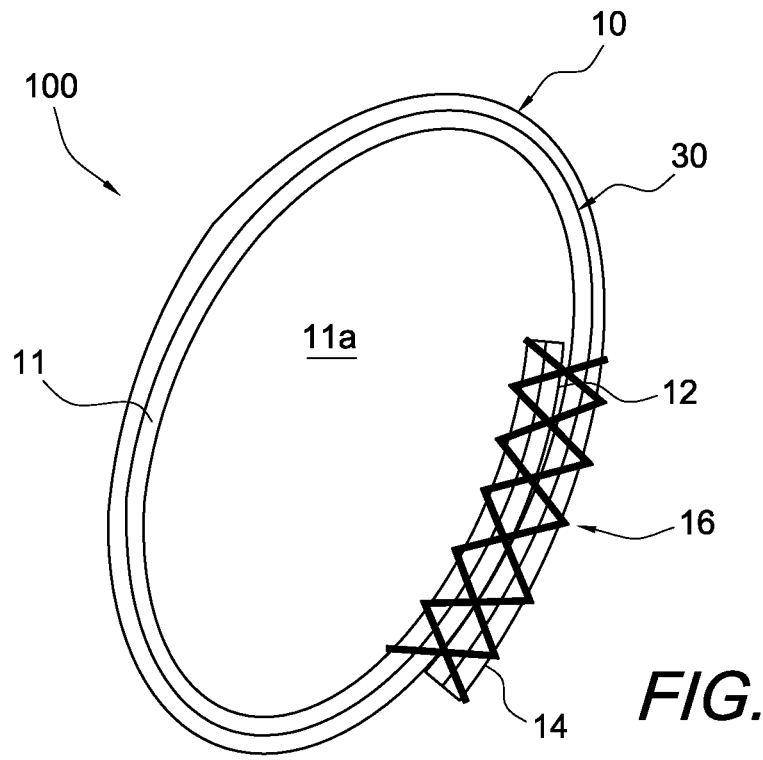
FIG. 3 illustrates just the reinforced continuous graft loop of the construct of FIG. 1 (with the ends of the graft stitched together in an overlapping manner).

FIG. 3 illustrates another view of reinforced loop construct 100 of the present invention including a loop of reinforced biological construct 11 but without any fixation devices attached. This type of reinforced graft loop construct could be used as shown in FIG. 5B with a transfix or cross-pin type fixation device 300. FIG. 3 illustrates looped reinforced construct 100 formed in an overlapping manner (i.e., with the two ends 12, 14 of the reinforced construct brought together by overlapping each other and then stitched together). The biological material 10 (for example, tendon, graft, ligament) is reinforced with a reinforcing material 30 such as suture, Fiberwire®, FiberTape®, absorbable suture, tape or any other material or combination of such materials to form reinforced biological construct 11. Once the ends 12, 14 of the reinforced construct 11 are brought together in an overlapping manner, stitching such as whipstitching or other securing stitch with suture such as #$_2$ Fiberwire®, for example, may be conducted as detailed above with reference to FIGS. 2A-2G to form stitched loop region 16. The reinforcement suture may be tied to create additional reinforcement.

Figure 4:
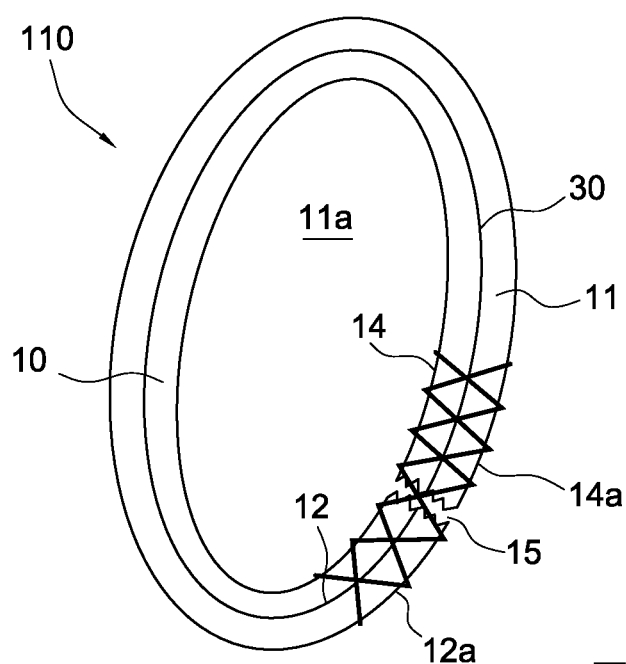
FIG. 4 illustrates an alternate embodiment of a reinforced continuous graft loop of the present invention, where the ends of the graft are stitched together in a non-overlapping manner.

In another alternate embodiment of the present invention as illustrated in FIG. 4, the first and second ends 12, 14 of the biological construct 10 may be attached without overlapping to form reinforced loop construct 110. A suture or tape 30 is still inserted longitudinally along the biological construct 10 (i.e., tendon 10) prior to forming the loop 11a, and to form reinforced biological construct 11. Stitching is done on each of the ends 12, 14 through the longitudinal suture or tape 30 to create reinforced sections 12a, 14a at each end 12, 14 which are then stitched together at the ends instead of overlapping (i.e., the most proximal and most distal ends of the reinforced biological construct 11 are brought together and adjacent to each other by suturing or stitching to form stitched region 15). The reinforcing suture 30 may be tied to create additional reinforcement.

Figure 5A:
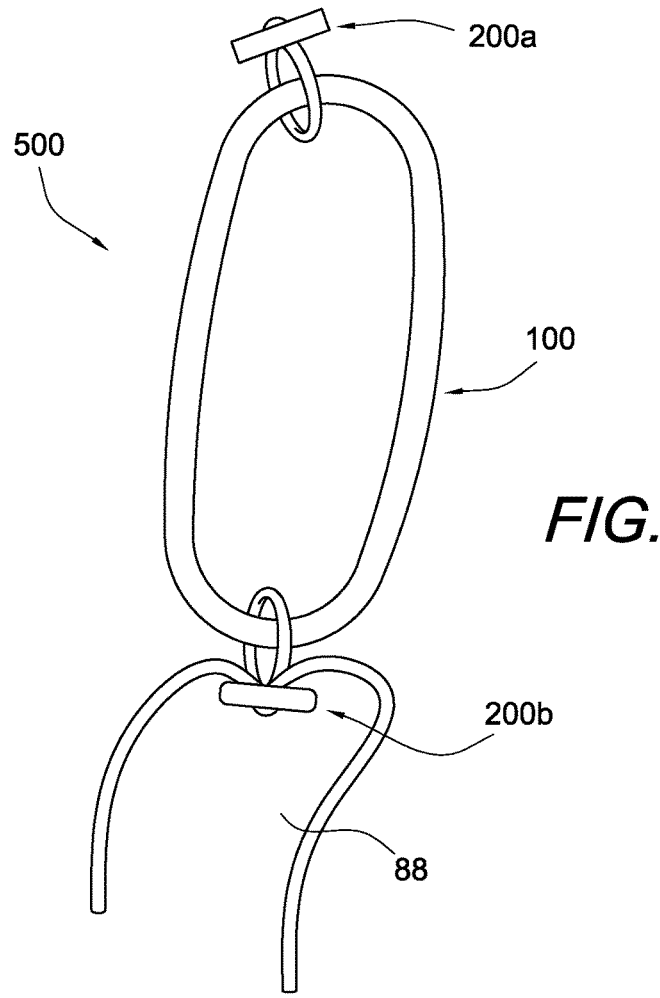
FIG. 5A illustrates another view of the reinforced assembly of FIG. 1 with one of the fixation devices attached to the tibia.
Figure 5B:
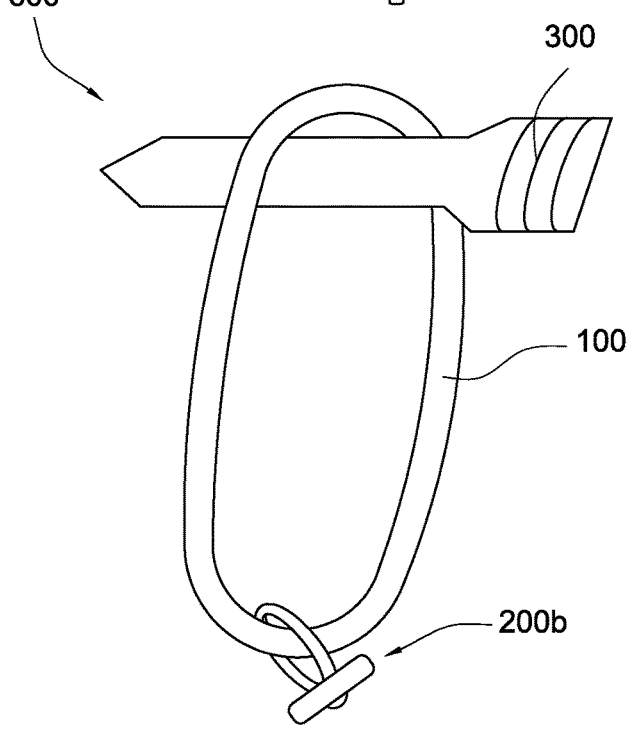
FIG. 5B illustrates an alternate embodiment of a reinforced assembly of the present invention with a reinforced continuous graft loop construct and a cross-pin fixation device.

FIG. 5A illustrates another view of the reinforced assembly 500 of FIG. 1 (comprising reinforced loop construct 100 and two fixation devices 200a, 200b attached thereto or inserted onto it) but with fixation device 200b secured to tibia 88, in a method of ACL repair with fixation at both ends. Fixation device 200a may be secured to the femur. At least one of the fixation devices 200a, 200b may be a RetroButton® or other button with a suture loop for attachment to the femoral side, or a an adjustable loop with button such as an ACL Tightrope® (or other adjustable button and suture construct), for the tibial and/or femoral side fixation and passed over the graft.

FIG. 5B illustrates a reinforced assembly 600 with reinforced loop construct 100 used with a transfix or cross-pin type fixation device 300 (or other rigid pin-type fixation device). A fixation device 200b such as a RetroButton®, ACL Tightrope® or other suture loop/button construct may be attached to the reinforced loop construct 100 to secure attachment to the tibial side.

Figure 6:
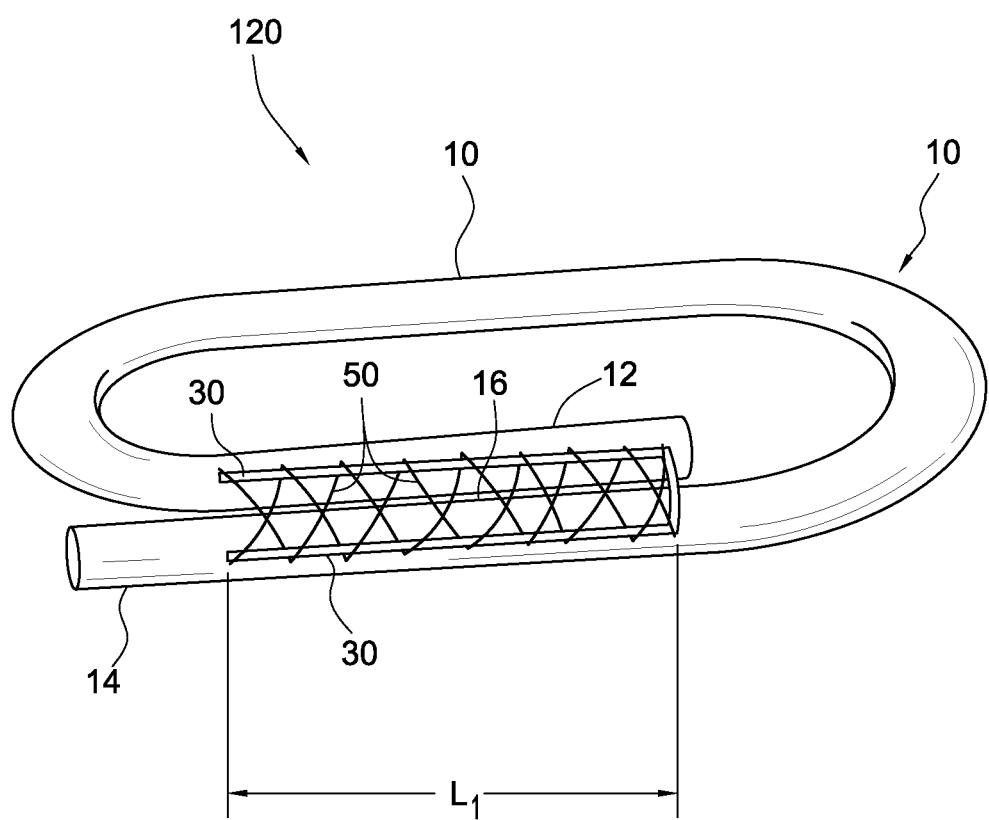
FIG. 6 illustrates an alternate embodiment of a reinforced continuous graft loop where only the whipstitched portion of the loop is reinforced.

An alternate method of constructing reinforced loop construct 120 of FIG. 6 follows the steps outlined in FIGS. 2A-2G, however, instead of inserting the reinforcement material 30 (suture or tape 30) through the entire biological construct 10 (graft, ligament or tendon 10) lengthwise, a small needle with the suture or tape is passed lengthwise through only a portion of the biological construct 10 on the first end 12 and the second end 14, preferably the end portions of the biological construct 10 (tendon 10) that will overlap. Whipstitching (with a suture such as #2 Fiberwire®) is conducted through the section 16 containing the lengthwise suture or tape 30 to attach the overlapping ends 12, 14 of the graft 10 to form stitched/sutured area of the reinforced loop construct 120. In this embodiment shown in FIG. 6, only the ends 12, 14 of the graft loop are reinforced (with reinforced suture or tape 30 such as FiberTape or absorbable tape material inserted only through the ends 12, 14 of the tendon 10), and not the whole length of the tendon (i.e., not the tendon portion extending between the two ends 12, 14).

In the specific embodiment shown in FIG. 6, the reinforced stitched region 16 contains two overlapped ends of the reinforced biological construct with two sections of reinforcement material 30 (suture or tape 30) each of the two sections being passed through a respective one of the two ends (to form two reinforced ends), and further with the two reinforced ends sutured/stitched together to form stitched/sutured area 50. However, the invention also contemplates embodiments wherein the reinforced stitched region contains two overlapped ends of the reinforced biological construct with only one section of reinforcement material 30 (i.e., only one section of suture or tape 30) passed through only one of the two ends, and further with the ends sutured/stitched together. The length L1 of each of the ends 12, 14 with reinforcement material 30 may be about ⅕ to about ¼ of the total length L of the biological construct 10.

Figure 7:
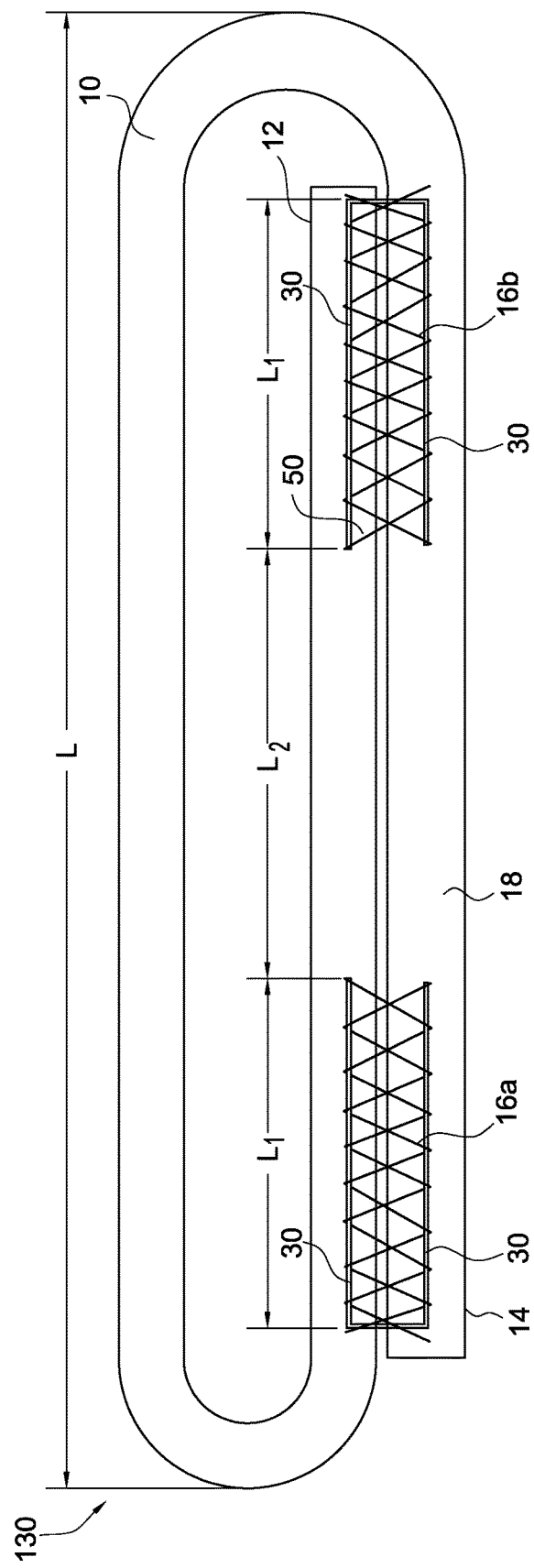
FIG. 7 illustrates an alternate embodiment of a reinforced continuous graft loop having two reinforced whipstitched sections separated by a smooth unstitched section.

Reference is now made to FIG. 7. In an alternate method of constructing a reinforced loop construct 130, the construct may be separated into three zones, including two reinforced areas 16a, 16 b (for example, two whipstitched areas 16a, 16b of biological construct) and one zone 18 of bare biological construct (tendon) (smooth unstitched portion) between the other two zones. This construct may be beneficial in an all-inside procedure (patient specific) such as an all-inside ACL reconstruction when placing the whipstitched zones of the construct into bone sockets, such as the femoral and tibial sockets, while the unstitched zone can be in contact with the articulating surfaces of the bone. This prevents irritation between the articulating surfaces due to the presence of stitching. FIG. 7 illustrates this embodiment where the reinforced whipstitched sections 16a, 16b are separated by an unstitched section 18.

Each of the reinforced whipstitched sections 16a, 16b contains two sections of reinforcement material 30 (suture or tape 30), each section of reinforcement material 30 being passed through a respective section of one of the two ends 12, 14. Each of the reinforced whipstitched sections 16a, 16b also contains a stitched (sutured) area 50 formed with a flexible material such as suture. Reinforcement material 30 (suture or tape 30) may be inserted along the length of each end and centered with respect to the longitudinal axis of the biological construct 10 (tendon 10). The final reinforced construct 130 includes four sections of reinforcement material 30 (suture or tape 30) inserted along the length of two regions of ends 12, 14 that are brought together (in an overlapping manner) and stitched with additional flexible material such as suture.

The two reinforced whipstitched sections 16a, 16b may have the same length or different lengths as determined by the depth of the sockets created in the reconstruction procedure. This construct allows for adjustability for each patient based on the actual socket size created during the surgery. In an exemplary embodiment only, length L1 of the reinforced whipstitched sections 16a, 16b may be about equal to length L2 of the bare section 18 (smooth unstitched section 18) and about ⅓ to about ¼ of the total length L of the reinforced construct 130. In an exemplary embodiment only, length L1 may be about 20 mm and length L2 may be about 20-30 mm, while length L may be about 90-120 mm.

FIGS. 8A-8D illustrate exemplary steps of the method of creating the construct of FIG. 7.

Figure 8A:
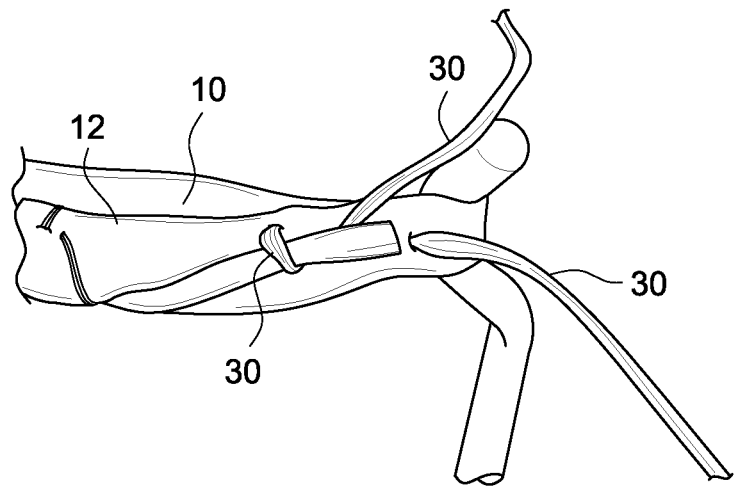
FIGS. 8A-D illustrate a method of preparing the reinforced continuous graft loop of FIG. 7.

FIG. 8A: The reinforcing material 30 (FiberTape®) is passed lengthwise into and out of the free end of the tendon, and then inserted into the portion of the tendon loop that is alongside the free end, creating a "U-shape" with the reinforcing material 30. A shown in FIG. 8A, the second zone of reinforced whipstitching is created by inserting reinforcing material 30 (suture or tape 30) through one end 12 of the biological construct 10 (tendon 10) lengthwise to the end of the tendon and then inserting the same reinforcing material 30 (suture or tape 30) into the overlapping section of the tendon lengthwise a distance determined to correlate to the depth of the socket or tunnel. The distance may be in the range of 20-30 mm. The reinforcing material 30 (suture 30) forms a U-shape in the tendon.

Figure 8B:
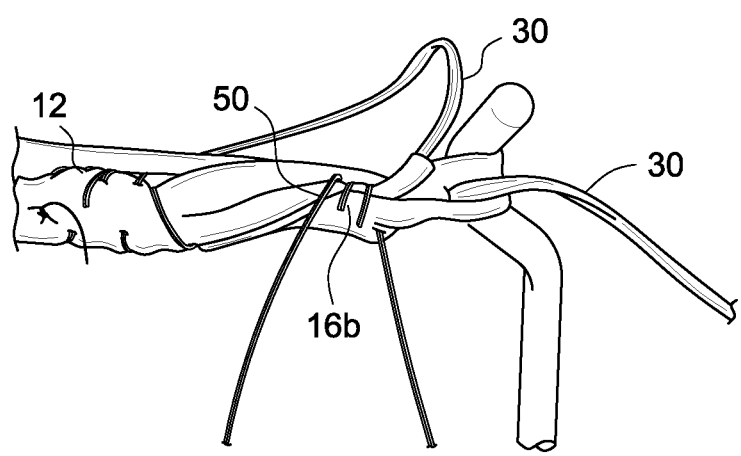

FIG. 8B: A single stand of flexible material (for example, #2 Fiberwire®) is used to begin the whipstitching. It is not necessary to pierce the reinforcing material 30 (FiberTape® 30) with every pass, although it is helpful to use the visible portions of the FiberTape® for the first several stitches. In FIG. 8B, another flexible strand 50 (suture 50) is used to whipstitch the overlapping sections of the tendon together through the reinforcing material 30 (suture 30) to create a zone of reinforced whipstitching 16b.

Figure 8C:
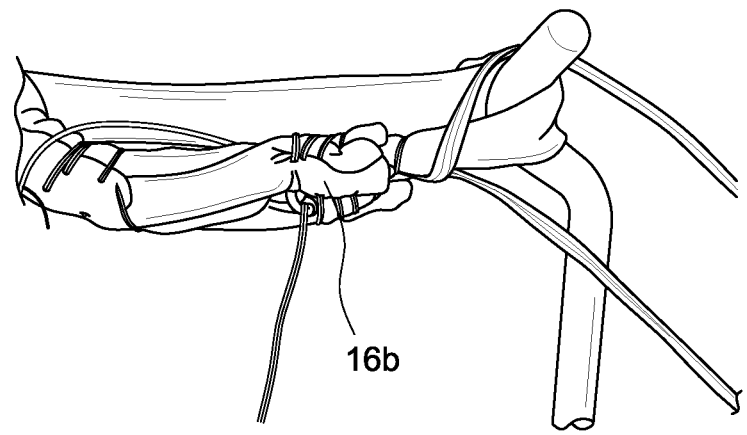

FIG. 8C: Whipstitching is continued down the opposite side of the graft.

Figure 8D:
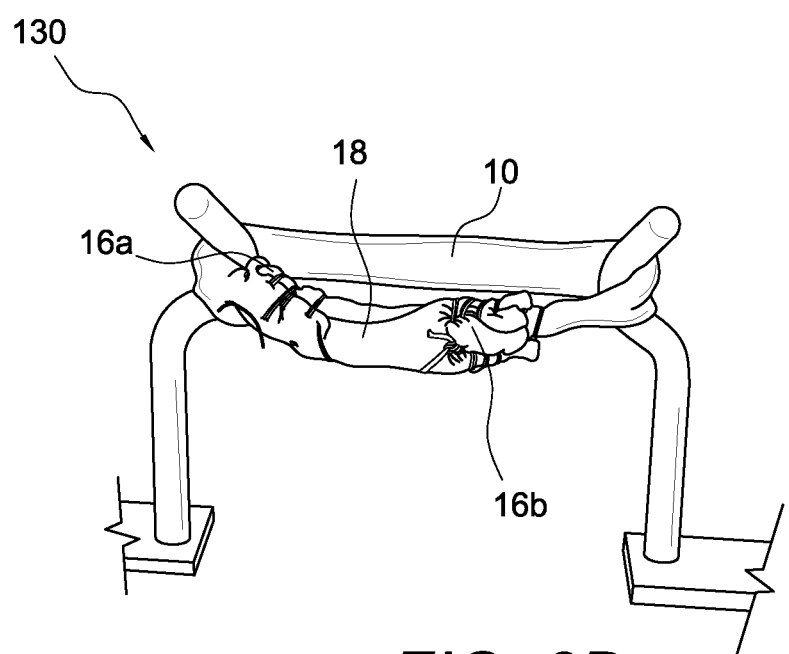

FIG. 8D: The free ends of the Fiberwire® are knotted to secure the stitch. FIG. 8D illustrates the final construct with reinforced whipstitched zones 16a, 16b and the stitch-free zone 18 (smooth unstitched section 18).

Figure 9A:
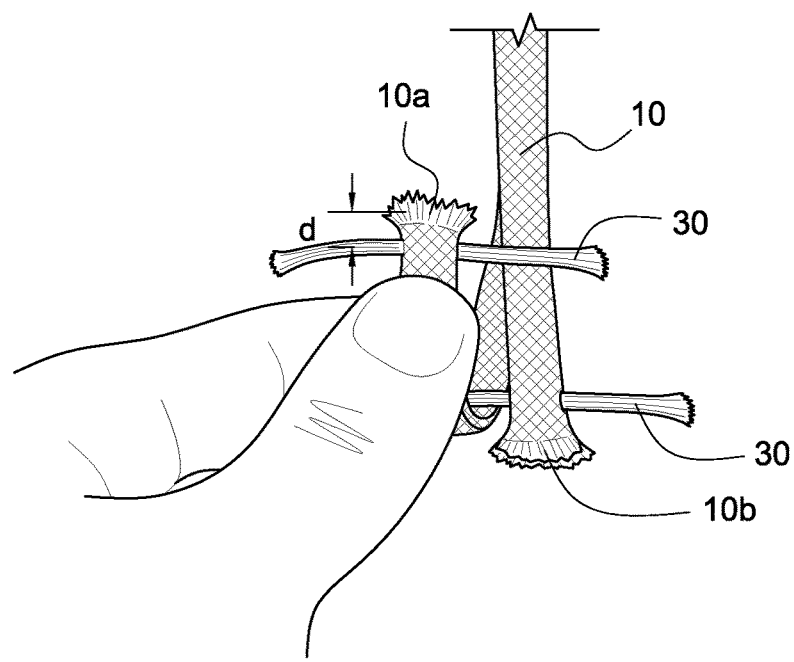
FIGS. 9A-C illustrate a method of reinforcing a torn ligament or tendon in situ and according to another embodiment of the present invention.
Figure 9B:
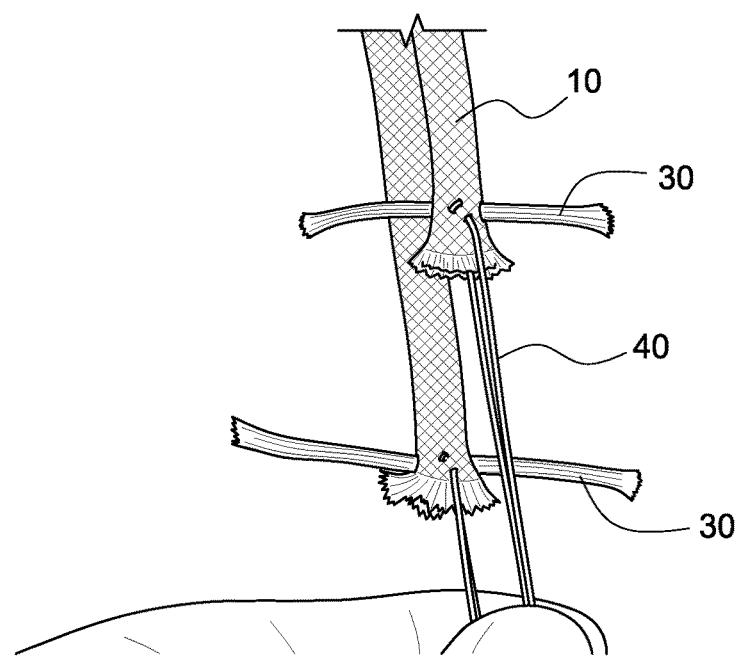
Figure 9C:
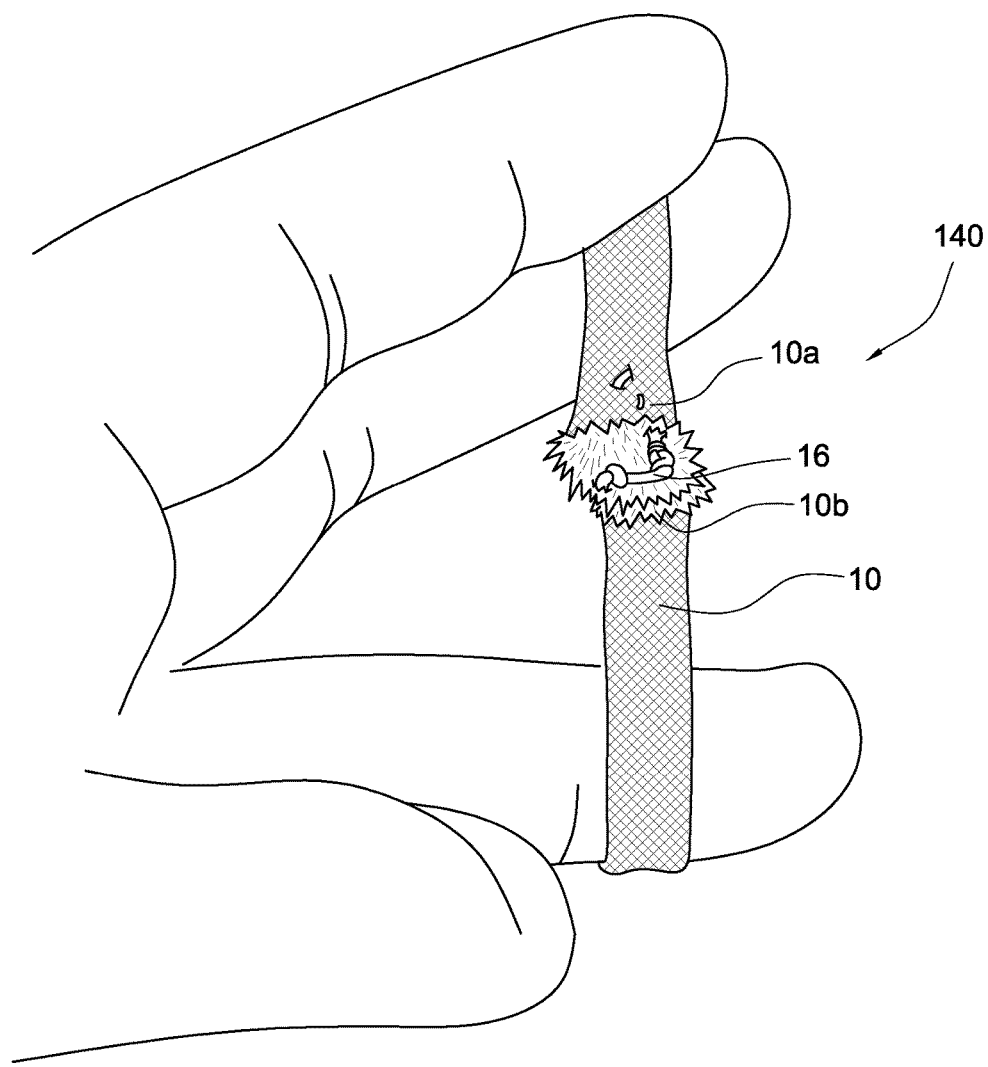

An exemplary technique for repairing a tendon or ligament that is torn within the body without using a graft includes reinforcing the torn tendon or ligament within the body and at the injury repair site (i.e., in situ). One method for reinforcing torn tendon 10 is illustrated in FIGS. 9A-C. FIG. 9A shows inserting a reinforcement material 30 (for example, a suture type material 30) in a direction about parallel to each torn edge 10a, 10b of the torn tendon 10 and a short distance "d" of about 1-4 mm from the edge of the tendon 10. In this embodiment, the reinforcement material 30 is not inserted along the longitudinal axis of the construct (i.e., in a direction parallel to the longitudinal axis) but rather in a direction about perpendicular to the longitudinal axis of the construct.

Another length of reinforcement material 40 (for example, a suture or similar type material) is passed through the ends 10a, 10b of the torn tendon 10 and also through the previously-inserted reinforcement material 30 (i.e., suture material 30). FIG. 9B illustrates a mattress stitch being applied through the reinforced end of the torn tendon. The same steps are repeated on the other torn end of the tendon.

FIG. 9C illustrates the two reinforced torn ends 10a, 10b of the tendon stitched back together in stitched reinforced area 16 to complete the repair and form reinforced tendon construct 140.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, the invention is not to be considered as limited by the foregoing description.

What is claimed is:

1. A method of reinforcing a biological construct, comprising:

inserting a reinforcement material longitudinally through a biological construct such that the reinforcement material enters the biological construct at a first location and exits the biological construct at a second location that is longitudinally spaced from the first location, wherein the biological construct is at least one of a tendon or a ligament and the reinforcement material is one of a suture, a tape, a weave, a mesh, or combinations of a suture, a tape, a weave, and a mesh; and stitching together portions of the biological construct containing the reinforcement material to form a reinforced biological construct, wherein the stitching is performed using a flexible strand that is separate from the reinforcement material.

2. The method of claim 1, wherein the step of passing a reinforcement material longitudinally through at least a portion of the biological construct comprises:

inserting a first reinforcement material through each of a first end and a second end of a torn tendon or ligament, in a direction parallel to each of the torn edges of the torn tendon or ligament, and spaced apart from a most distal end of each of the edges of the torn tendon or ligament;

subsequently, inserting a second reinforcement material through each of the first end and second end of a torn tendon or ligament, and through the first reinforcement material; and stitching back together the first and second ends to form a reconstructed torn tendon or ligament.

3. The method of claim 2, wherein at least one of the first and second reinforcement material is a suture material or suture tape.

4. The method of claim 2, wherein the first reinforcement material is a suture tape and the second reinforcement material is a suture strand.

5. The method of claim 2, wherein the method is conducted in situ.

6. The method of claim 1, further comprising the step of:
attaching at least one fixation device to the reinforced biological construct.

7. The method of claim 1, wherein the stitching together is a first end and a second end of the reinforced biological construct stitched together to form a reinforced looped biological construct.

8. The method of claim 1, wherein stitching together the portions of the biological construct includes passing a suture through both the biological construct and the reinforcement material.

9. The method of claim 8, comprising using a needle to pass the suture.

10. The method of claim 1, wherein the first location is within a first end of the biological construct and the second location is within a second end of the biological construct.

11. The method of claim 1, wherein inserting the reinforcement material includes pulling the reinforcement material through the biological construct using a passing wire.

12. The method of claim 1, comprising securing the biological construct within a prep-station prior to inserting the reinforcement material.

13. The method of claim 1, comprising:

inserting a fixation device onto the reinforced biological construct;

doubling the reinforced biological construct over so a first end and a second end of the reinforced biological construct overlap one another; and stitching the first end and the second end together to create a reinforced looped biological construct.

14. The method of claim 13, comprising pretensioning the reinforced looped biological construct prior to using the reinforced looped biological construct in a tissue repair procedure.

15. The method of claim 1, wherein stitching together the portions of the biological construct includes whipstitching the biological construct.

16. The method of claim 15, comprising completing the whipstitching by forming a knot to create a stitched looped region.

17. The method of claim 1, wherein stitching together the portions of the biological construct includes:

overlapping a first end and a second end of the biological construct; and stitching the first end and the second end together using a needle and a suture.

18. A method of reinforcing a biological construct, comprising:

inserting a passing wire through the biological construct, wherein the biological construct is at least one of a tendon or a ligament;

connecting a reinforcement material to the passing wire;

pulling the reinforcement material through the biological construct using the passing wire such that the reinforcement material enters and exits the biological construct at longitudinally spaced locations; and stitching together portions of the biological construct containing the reinforcement material using a flexible strand that is separate from the reinforcement material.

19. A method of reinforcing a biological construct, comprising:

inserting a reinforcement material longitudinally through the biological construct to create a reinforced biological construct, the reinforcement material entering the biological construct within a first end portion and exiting the biological construct within a second end portion, wherein the biological construct is at least one of a tendon or a ligament;

folding the reinforced biological construct over so the first end portion and the second end portion overlap; and stitching the first end portion and the second end portion together to create a reinforced looped biological construct.

* * * * *